US010961582B2

(12) United States Patent
Noth et al.

(10) Patent No.: US 10,961,582 B2
(45) Date of Patent: Mar. 30, 2021

(54) BIOMARKERS FOR ASSESSING IDIOPATHIC PULMONARY FIBROSIS

(71) Applicants: The University of Chicago, Chicago, IL (US); The Board of Trustees of the University of Illinois, Urbana, IL (US); University of Pittsburgh—Of the Commonwealth System of Higher Education, Pittsburgh, PA (US)

(72) Inventors: Imre Noth, Chicago, IL (US); Yong Huang, Dyer, IN (US); Jose David Herazo-Maya, North Haven, CT (US); Naftali Kaminski, New Haven, CT (US); Kevin Gibson, Gibsonia, PA (US); Joe G. N. Garcia, Tucson, AZ (US)

(73) Assignees: The University of Chicago, Chicago, IL (US); The Board of Trustees of the University of Illinois, Urbana, IL (US); University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 16/031,384

(22) Filed: Jul. 10, 2018

(65) Prior Publication Data
US 2018/0320234 A1 Nov. 8, 2018

Related U.S. Application Data

(62) Division of application No. 14/358,945, filed as application No. PCT/US2012/065540 on Nov. 16, 2012, now Pat. No. 10,036,069.

(60) Provisional application No. 61/561,543, filed on Nov. 18, 2011.

(51) Int. Cl.
C12Q 1/68 (2018.01)
C12Q 1/6883 (2018.01)
G01N 33/569 (2006.01)

(52) U.S. Cl.
CPC ..... *C12Q 1/6883* (2013.01); *G01N 33/56966* (2013.01); *C12Q 2600/118* (2013.01)

(58) Field of Classification Search
None
See application file for complete search history.

(56) References Cited

PUBLICATIONS

Herazo et al; Am J Respir Crit Care Med, vol. 183, May 2011, abstract.*

Achiron A, Gurevich M, Friedman N, Kaminski N, Mandel M. Blood transcriptional signatures of multiple sclerosis: unique gene expression of disease activity. *Annals of Neurology* 2004, 55(3): 410-7.
American Thoracic S, European Respiratory S. American Thoracic Society/European Respiratory Society International Multidisciplinary Consensus Classification of the Idiopathic Interstitial Pneumonias. This joint statement of the American Thoracic Society (ATS), and the European Respiratory Society (ERS) was adopted by the ATS board of directors, Jun. 2001 and by the ERS Executive Committee, Jun. 2001. *American Journal of Respiratory and Critical Care Medicine* 2002; 165(2): 277-304.
Baine MJ, Chakraborty S, Smith LM, et al. Transcriptional profiling of peripheral blood mononuclear cells in pancreatic cancer patients identifies novel genes with potential diagnostic utility. *PloS one* 2011; 6(2): e17014.
Bluth M, Lin YY, Zhang H, Viterbo D, Zenilman M. Use of gene expression profiles in cells of peripheral blood to identify new molecular markers of acute pancreatitis. *Arch Surg* 2008, 143(3): 227-33; discussion 33-4.
Bull TM, Coldren CD, Nana-Sinkam P, et al. Microarray analysis of peripheral blood cells in pulmonary arterial hypertension, surrogate to biopsy. *Chest* 2005, 128(6 Suppl): 584S.
du Bois RM, Weycker D, Albera C, et al. Forced Vital capacity in patients with idiopathic pulmonary fibrosis: test properties and minimal clinically important difference. *American Journal of Respiratory and Critical Care Medicine* 2011; 184(12): 1382-9.
Efron B, Tibshirani R. On testing the significance of set of genes. *Ann App Stat* 2007; 1(1): 107-29.
Egan TM, Murray S, Bustami RT, et al. Development of the new lung allocation system in the United States. *Am J Transplant* 2006; 6(5 Pt 2): 1212-27.
Feghali-Bostwick CA, Tsai CG, Valentine VG, et al. Cellular and humoral autoreactivity in idiopathic pulmonary fibrosis. *J Immunol* 2007; 179(4): 2592-9.
Fernandez Perez ER, Daniels CE, Schroeder DR, et al. Incidence, prevalence, and clinical course of idiopathic pulmonary fibrosis: a population-based study. *Chest* 2010; 137(1): 129-37.
Gilani SR, Vuga LJ, Lindell KO, et al. CD28 down-regulation on circulating CD4 T-cells is associated with poor prognoses of patients with idiopathic pulmonary fibrosis. *PloS one* 2010; 5(1): e8959.
Herazo-Maya JD, Kaminski N. Personalized medicine: applying 'omics' to lung fibrosis. *Biomarkers in Medicine* 2012; 6(4): 529-40.
Hoon, Cluster 3.0 for Windows, Mac OS X, Linux, Unix, Human Genome Center, University of Tokyo, 2002. http://bonsai.hgc.jp/~mdehoon/software/cluster/manual. Retrieved on Jul. 30, 2015.
Ihaka R GR. A language for data analysis and graphics. *J Comput Graph Statist* 1996; 5: 299-314.
International Preliminary Report on Patentability for PCT/US2012/065540, dated May 20, 2014.
Irizarry RA, Hobbs B, Collin F, et al. Exploration, normalization, and summaries of high density oligonucleotide array probe level data. *Biostatistics (Oxford, England)* 2003; 4(2): 249-64.
Kinder BW, Brown KK, McCormack FX, et al. Serum surfactant protein-A is a strong predictor of early mortality in idiopathic pulmonary fibrosis. *Chest* 2009; 135(6): 1557-63.
King TE, Jr., Tooze JA, Schwarz MI, Brown KR, Cherniack RM. Predicting survival in idiopathic pulmonary fibrosis: scoring system and survival model. *American journal of respiratory and critical care medicine* 2001; 164(7): 1171-81.

(Continued)

*Primary Examiner* — Jehanne S Sitton
(74) *Attorney, Agent, or Firm* — Norton Rose Fulbright US LLP

(57) ABSTRACT

Disclosed are methods and kits for evaluating predicting whether an individual IPF has slowly or rapidly progressive IPF.

12 Claims, 4 Drawing Sheets

(56) References Cited

PUBLICATIONS

Ley B, Collard HR, King TE, Jr. Clinical course and prediction of survival in idiopathic pulmonary fibrosis. *American journal of respiratory and critical care medicine* 2011; 183(4): 431-40.

Moeller A, Gilpin SE, Ask K, et al. Circulating fibrocytes are an indicator of poor prognosis in idiopathic pulmonary fibrosis. *American journal of respiratory and critical care medicine* 2009; 179(7): 588-94.

Moore DF, Li H, Jeffries N, et al. Using peripheral blood mononuclear cells to determine a gene expression profile of acute ischemic stroke: a pilot investigation. *Circulation* 2005; 111(2): 212-21.

Murphy SA, Van Der Vart AW. On Profile Likelihood. *Journal of the American Statistical Association* 2000; 95: 449-85.

Ottoboni L, Keenan BT, Tamayo P, et al. An RNA profile identifies two subsets of multiple sclerosis patients differing in disease activity. *Science translational medicine* 2012; 4(153): 153ra31.

Pham MX, Teuteberg JJ, Kfoury AG, et al. Gene-expression profiling for rejection surveillance after cardiac transplantation. *The New England journal of medicine* 2010; 362(20): 1890-900.

Prasse A, Probst C, Bargagli E, et al. Serum CC-chemokine ligand 18 concentration predicts outcome in idiopathic pulmonary fibrosis. *American journal of respiratory and critical care medicine* 2009; 179(8): 717-23.

Raghu G, Collard HR, Egan JJ, et al. An official ATS/ERS/JRS/ALAT statement: idiopathic pulmonary fibrosis: evidence-based guidelines for diagnosis and management. *American journal of respiratory and critical care medicine* 2011; 183(6): 788-824.

Richards TJ, Kaminski N, Baribaud F, et al. Peripheral blood proteins predict mortality in idiopathic pulmonary fibrosis. *American journal of respiratory and critical care medicine* 2012; 185(1): 67-76.

Risbano MG, Meadows CA, Coldren CD, et al. Altered immune phenotype in peripheral blood cells of patients with scleroderma-associated pulmonary hypertension. *Clin Transl Sci* 2010; 3(5): 210-8.

Rosas IO, Richards TJ, Konishi K, et al. MMP1 and MMP7 as potential peripheral blood biomarkers in idiopathic pulmonary fibrosis. *PLoS medicine* 2008; 5(4): e93.

Schwartz DA, Helmers RA, Galvin JR, et al. Determinants of survival in idiopathic pulmonary fibrosis. *American journal of respiratory and critical care medicine* 1994; 149(2 Pt 1): 450-4.

Segman RH, Shefi N, Goltser-Dubner T, Friedman N, Kaminski N, Shalev AY. Peripheral blood mononuclear cell gene expression profiles identify emergent post-traumatic stress disorder among trauma survivors. *Molecular psychiatry* 2005; 10(5): 500-13, 425.

Showe MK, Vachani A, Kossenkov AV, et al. Gene expression profiles in peripheral blood mononuclear cells can distinguish patients with non-small cell lung cancer from patients with non-malignant lung disease. *Cancer research* 2009; 69(24): 9202-10.

Therneau TM GP. Modeling survival data: extending the Cox model. New York: Springer; 2000.

Trulock EP, Edwards LB, Taylor DO, Boucek MM, Keck BM, Hertz MI. Registry of the International Society for Heart and Lung Transplantation: twenty-second official adult lung and heart-lung transplant report—2005. *J Heart Lung Transplant* 2005; 24(8): 956-67.

Tusher VG, Tibshirani R, Chu G. Significance analysis of microarrays applied to the ionizing radiation response. *Proceedings of the National Academy of Sciences of the United States of America* 2001; 98(9): 5116-21.

Venables WNR, B. D. Modern applied statistics with S. New York: Springer; 2002.

Wu W, Dave N, Tseng GC, Richards T, Xing EP, Kaminski N. Comparison of normalization methods for CodeLink Bioarray data. *BMC bioinformatics* 2005; 6: 309.

Xue J, Gochuico BR, Alawad AS, et al. The HLA class II Allele DRB1*1501 is over-represented in patients with idiopathic pulmonary fibrosis. *PLoS one* 2011; 6(2): e14715.

Yang IV, Luna LG, Cotter J, et al. The peripheral blood transcriptome identifies the presence and extent of disease in idiopathic pulmonary fibrosis. *PLoS one* 2012; 7(6): e37708.

Yokoyama A, Kondo K, Nakajima M, et al. Prognostic value of circulating KL-6 in idiopathic pulmonary fibrosis. *Respirology (Carlton, Vic* 2006; 11(2): 164-8.

Zahurak M, Parmigiani G, Yu W, et al. Pre-processing Agilent microarray data. *BMC bioinformatics* 2007; 8: 142.

Zappala CJ, Latsi PI, Nicholson AG, et al. Marginal decline in forced vital capacity is associated with a poor outcome in idiopathic pulmonary fibrosis. *Eur Respir J* 2010; 35(4): 830-6.

* cited by examiner

BIOMARKERS FOR ASSESSING IDIOPATHIC PULMONARY FIBROSIS

CROSS-REFERENCE TO RELATED APPLICATIONS

This application is a divisional of U.S. patent application Ser. No. 14/358,945 filed May 16, 2014, which is a national phase application under 35 U.S.C. § 371 of International Application No. PCT/US2012/065540 filed Nov. 16, 2012, which claims priority to U. S. Provisional Application Ser. No. 61/561,543, filed Nov. 18, 2011. The entire contents of each of the above-referenced disclosures are specifically incorporated herein by reference.

STATEMENT REGARDING FEDERALLY SPONSORED RESEARCH

This invention was made with government support under grant numbers HL080513, HL101740, and HL089493 awarded by the National Institutes of Health. The government has certain rights in the invention.

INTRODUCTION

Idiopathic Pulmonary Fibrosis (IPF) is a chronic and fatal lung disease for which the only therapy currently available is lung transplantation. The course of IPF is variable and unpredictable. There is thus a need in the art for methods of predicting prognosis of the disease in individuals affected by IPF.

BACKGROUND OF THE INVENTION

Idiopathic Pulmonary Fibrosis (IPF) is a chronic and progressive fibrosing interstitial lung disease with an unknown etiology. Diagnosis of IPF is based on clinical and radiological features and, when available, findings of usual interstitial pneumonia on lung biopsy. IPF patients have an overall median survival of 3-3.5 years. The disease is more prevalent and probably more lethal among males.[3, 4] With the exception of lung transplantation, no therapy has been proven beneficial for IPF.

The course of IPF is highly variable and largely unpredictable among individual patients. Disease progression in current clinical practice is monitored by pulmonary function tests [e.g., forced vital capacity (FVC), diffusion capacity for carbon monoxide (DLCO)]; high resolution CT scans (HRCT) and, measures of oxygenation. Previous studies have shown associations of serial measures of these clinical variables with disease extent and poor outcomes. The available evidence suggests that plasma protein concentrations and other blood cells may be of diagnostic use and to be indicative of disease severity and outcome prediction in IPF patients.

Identification of biomarkers may facilitate the diagnosis and follow-up of patients with IPF as well as the implementation of new therapeutic interventions. Currently, establishing a diagnosis of IPF may require surgical lung biopsy in patients with atypical clinical presentations or high-resolution computed tomography (HRCT) scans. Patients with IPF are often evaluated by serial pulmonary physiology measurements and repeated radiographic examinations. These studies provide a general assessment of the extent of disease, but do not provide information about disease activity on a molecular level. Higher plasma concentrations of surfactant proteins KL-6, FASL, CCL-2, α-defensins, and most recently SPP1 have been reported in patients with IPF and other ILDs but most of these studies were modest in size and assayed only a single or a few protein markers simultaneously. Matrix metalloproteinase-8 ("MMP8") has been implicated as playing a role in tissue remodeling in IPF, but also in sarcoidosis, making it a nonspecific marker of IPF. Similarly, matrix metalloproteinase-7 ("MMP7") was reported to be elevated in bronchoalveolar fluid from both IPF patients as well as patients suffering from cryptogenic organizing pneumonia ("COP").

More recently, certain panels of markers for diagnosing and evaluating the severity and/or progression of IPF have been proposed. Those panels are based, at least in part, on the discovery that identifying increases in the plasma levels of MMP7, MMP1 and MMP8, as well as IGFBP1 and/or TNFRSF1A, indicates a diagnosis of IPF with a high degree of sensitivity and specificity.

SUMMARY OF THE INVENTION

In one aspect, the present invention includes methods for assessing survival or poor outcome of the diseased individual with IPF. In some embodiments, the method involves measuring expression levels of a set of at least three of the markers listed in Table 1 and Table 2 in a sample from the individual and using the expression levels to predict survival in individual with IPF for the effective lung transplant therapy.

In another aspect, the present invention includes kits for performing the methods of the invention. The kits may comprise antibodies specific for each of the markers used in the methods or various primer pairs, each primer pair capable of amplifying one of the markers or a portion of the marker.

DETAILED DESCRIPTION OF THE INVENTION

Figure 1:
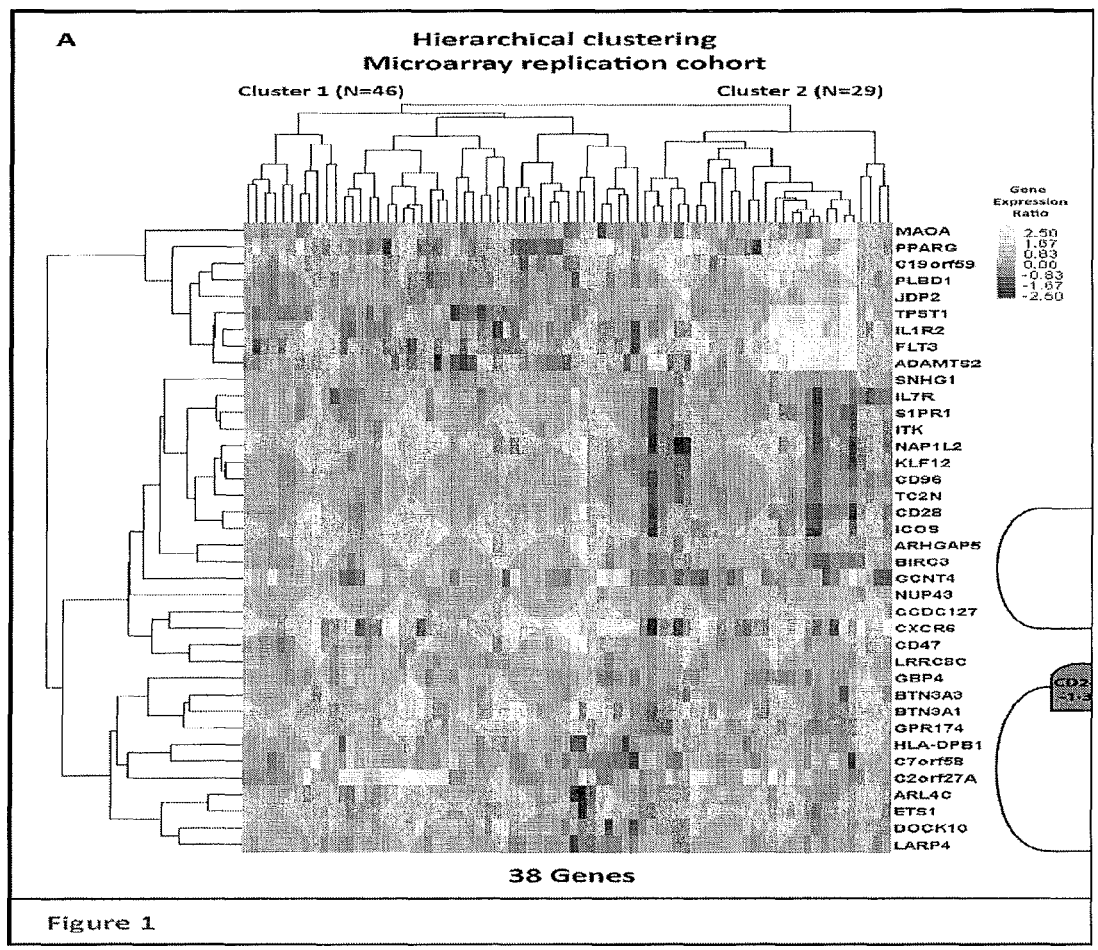
FIG. 1. (A) Heatmap depicting the hierarchical clustering of IPF subjects from the derivation cohort using the 38-gene signature found to be significantly associated with survival in the derivation cohort. Every row represents a gene and every column a patient. Color scale is shown adjacent to heatmap in log based 2 scale—generally, gray denotes increase over the geometric mean of samples and black decrease. Two major clusters of IPF patients were identified by this clustering technique. (B) Comparison of survival between the patients in the two major clusters. Kaplan-Meier survival estimate depicts a statistically significant difference in survival (P=0.006 by the Logrank test) between the 2 major clusters. (C) A diagram of the co-stimulatory signal during T cell activation pathway, genes colored in black are decreased, genes in gray are increased and genes in white are unchanged. The T cell receptor beta locus (TRBβ) gene is not colored since it was not included in the analyses as this probe was not common to both microarray platforms.
Figure 1:
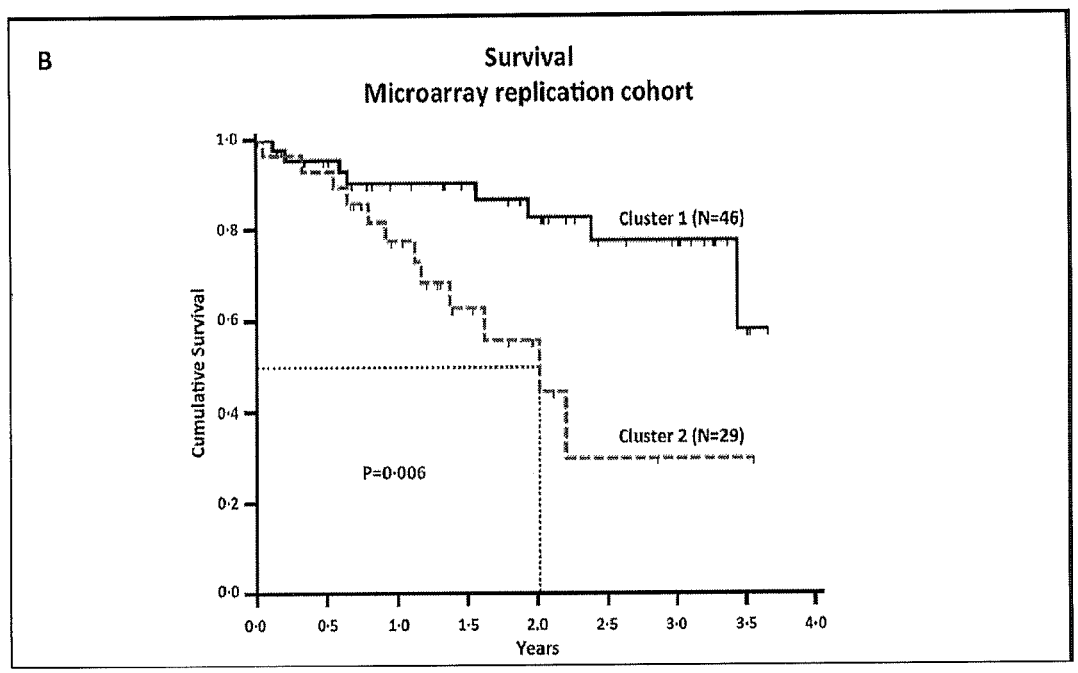
Figure 1:
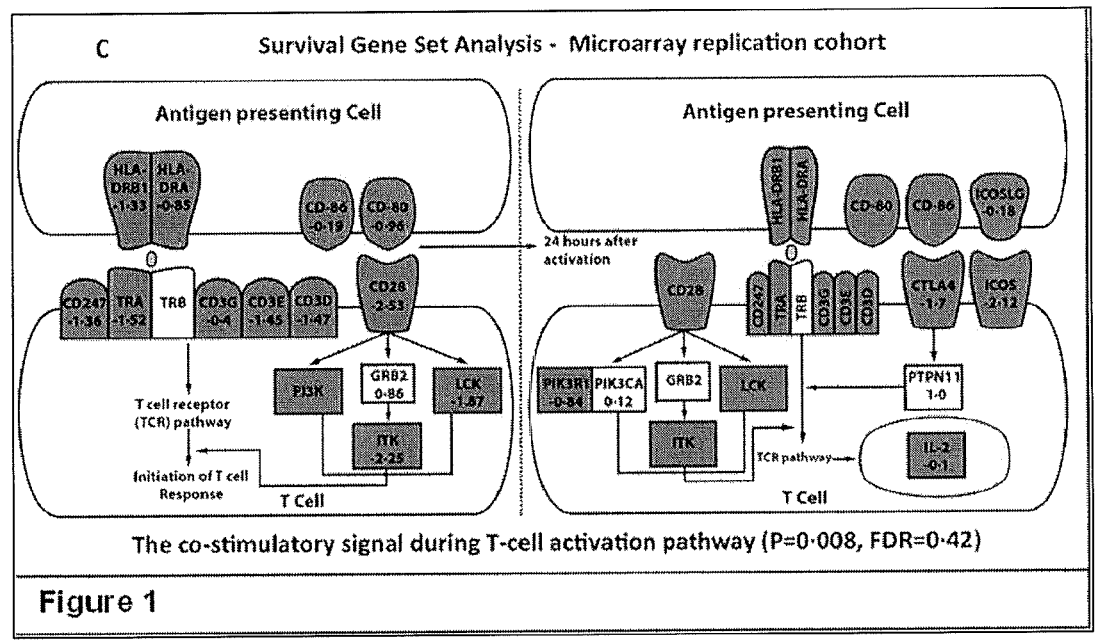

The present invention relates to methods and kits for diagnosing or evaluating the progression of IPF. As described below, two independent studies including individuals with IPF were conducted to identify genes the expression of which is correlated with overall survival. A matched gene expression dataset containing 17417 unique gene probes in each cohort was used for statistical analyses (see supplementary methods). A set of 217 gene-sets were analyzed by the gene set analysis (GSA) method. Of those genes, 38 (Table 1) were found to be significantly associated with survival in IPF patients and provided clues about potential biological process associated with survival in IPF with the co-stimulatory signal during T-cell activation pathway (Table 2). The expression products, i.e., RNA or protein products, of these 38 genes are also referred to herein as "biomarkers".

TABLE 1

Genes Associated with Survival

| Gene designation | Gene symbol | Cox |
|---|---|---|
| Peroxisome proliferator-activated receptor gamma | PPARG | 4.06 |
| Tyrosylprotein sulfotransferase 1 | TPST1 | 3.97 |
| Chromosome 19 open reading frame 59 (mast cell-expressed) | C19orf59 | 3.93 |
| Monoamine oxidase A | MAOA | 3.84 |
| Phospholipase B domain containing 1 | PLBD1 | 3.81 |
| Interleukin 1 receptor, type II | IL1R2 | 3.72 |
| ADAM metallopeptidase with thrombospondin type 1 motif, 2 | ADAMTS2 | 3.71 |
| Jun dimerization protein 2 | JDP2 | 3.70 |
| Fms-related tyrosine kinase 3 | FLT3 | 3.64 |
| Nucleosome assembly protein 1-like 2 | NAP1L2 | −4.23 |
| Interleukin 7 receptor | IL7R | −4.04 |
| Kruppel-like factor 12 | KLF12 | −3.95 |
| Sphingosine-1-phosphate receptor 1 | S1PR1 | −3.84 |
| Small nucleolar RNA host gene 1 | SNHG1 | −3.83 |
| Guanylate binding protein 4 | GBP4 | −3.73 |
| CD96 molecule | CD96 | −3.71 |
| Coiled-coil domain containing 127 | CCDC127 | −3.65 |
| Chemokine (C-X-C motif) receptor 6 | CXCR6 | −3.64 |
| IL2 inducible T cell kinase | ITK | −3.63 |
| Butyrophilin, subfamily 3, member A3 | BTN3A3 | −3.60 |
| Major histocompatibility complex, class II, DP beta 1 | HLA-DPB1 | −3.55 |
| Dedicator of cytokinesis 10 | DOCK10 | −3.53 |
| CD28 molecule | CD28 | −3.50 |
| Cadherin-like and PC-esterase domain containing 1 | CPED1 | −3.49 |
| ADP-ribosylation factor-like 4C | ARL4C | −3.46 |
| Rho GTPase activating protein 5 | ARHGAP5 | −3.46 |
| Glucosaminyl (N-acetyl) transferase 4, core 2 | GCNT4 | −3.43 |
| Tandem C2 domains, nuclear | TC2N | −3.42 |
| Butyrophilin, subfamily 3, member A1 | BTN3A1 | −3.41 |
| V-ets erythroblastosis virus E26 oncogene homolog 1 | ETS1 | −3.40 |
| CD47 molecule | CD47 | −3.40 |
| Baculoviral IAP repeat containing 3 | BIRC3 | −3.39 |
| Chromosome 2 open reading frame 27A | C2orf27A | −3.39 |

TABLE 1-continued

Genes Associated with Survival

| Gene designation | Gene symbol | Cox |
|---|---|---|
| Leucine rich repeat containing 8 family, member C | LRRC8C | −3.38 |
| Nucleoporin 43 kDa | NUP43 | −3.36 |
| G protein-coupled receptor 174 | GPR174 | −3.36 |
| Inducible T cell co-stimulator | ICOS | −3.35 |
| La ribonucleoprotein domain family, member 4 | LARP4 | −3.34 |

It is envisioned that assessing expression of any subset of the 38 biomarkers in an individual with IPF will allow one to predict whether the disease is likely to have poor outcome. For example, as described below, a decrease in expression of CD28, ITK, ICOS, or LCK was found to be predictive of earlier mortality in patients with IPF.

TABLE 2

Signature Associated with Survival

| Gene designation | Gene symbol | Cox |
|---|---|---|
| IL2 inducible T cell kinase | ITK | −3.56 |
| CD28 molecule | CD28 | −3.42 |
| Inducible T cell co-stimulator | ICOS | −3.32 |
| Lymphocyte-specific protein tyrosine kinase | LCK | −3.17 |
| CD86 molecule | CD86 | −3.09 |
| CD3g molecule, gamma (CD3-TCR complex) | CD3G | −2.92 |
| CD247 molecule | CD247 | −2.87 |
| Phosphoinositide-3-kinase, regulatory subunit 1 (alpha) | PIK3R1 | −2.74 |
| Major histocompatibility complex, class II, DR beta 1 | HLA-DRB1 | −2.73 |
| Major histocompatibility complex, class II, DR alpha | HLA-DRA | −2.60 |
| T cell receptor alpha locus | TRAα | −2.55 |
| CD3d molecule, delta (CD3-TCR complex) | CD3D | −2.23 |
| Phosphatidylinositol-4,5-bisphosphate 3-kinase, catalytic subunit | PIK3CA | −2.20 |
| CD3e molecule, epsilon (CD3-TCR complex) | CD3E | −2.18 |
| Cytotoxic T-lymphocyte-associated protein 4 | CTLA4 | −2.00 |
| Protein tyrosine phosphatase, non-receptor type 11 | PTPN11 | −1.03 |
| Interleukin 2 | IL2 | −0.93 |
| CD80 molecule | CD80 | 0.13 |
| Inducible T-cell co-stimulator ligand | ICOSLG | 0.40 |
| Growth factor receptor-bound protein 2 | GRB2 | 1.30 |

As used herein, "patients with poor prognostic IPF" is used interchangeably with "patients with rapidly progressive IPF". These patients are expected to have early mortality, relative to patients with good prognostic IPF or slowly progressive IPF. In general, this subpopulation of IPF patients can be expected to die within 18 months of analysis assuming that they do not receive lung transplants. Patients with good prognostic IPF or slowly progressive IPF are expected to have relatively late mortality, and can be expected to live more than 18-30 months after testing.

In the examples below, differentially expressed genes were identified in peripheral blood mononuclear cells (PBMCs) at the level of RNA expression by hybridization of cRNA to microarrays or indirectly by quantitative reverse transcription polymerase chain reaction ((qRT-PCR). Any suitable method of assaying relative or absolute RNA expression levels may be used in the methods of the invention. Additionally, it is envisioned that the relative or absolute levels of expression of the protein products of the differentially expressed genes may be used in the methods of the invention, using any suitable method of detection, including, for example, ELISA or Western blots.

Further, whether expression of a biomarker in a sample is "increased" or "decreased" may be determined by comparing the expression level in that sample to expression levels obtained from a plurality of samples taken from a population of individuals with IPF that includes both individuals with rapidly progressive IPF and individuals with slowly progressive IPF, for example, by comparing the expression level in a sample to the median value for that gene in a population of individuals with IPF. Additionally, or alternatively, increased or decreased expression of a particular biomarker may be evaluated using gene normalization. Although relative expression levels were used in the examples, one could readily establish ranges of expression levels for each of the tested biomarkers correlated with slowly or rapidly progressive IPF.

Although PBMCs may be conveniently used in the methods of the invention, it is expected that one or more of the biomarkers may be assayed in plasma or serum samples.

In one set of non-limiting embodiments, the panel comprises of a set of at least three of the markers listed in Table 1 and Table 2. In particular non-limiting embodiments, markers in the panel include CD28, ITK, ICOS, or LCK. In another particular non-limiting embodiment, markers in the panel include PPARG, TPST1, or MCEMP1. In another set of non-limiting embodiments, the panel comprises of a set of at least five of the markers listed in Table 1 and Table 2. In particular non-limiting embodiments, markers in the panel include CD28, ITK, ICOS, or LCK. In another particular non-limiting embodiment, markers in the panel include PPARG, TPST1, or MCEMP1.

In a first set of non-limiting embodiments, the present invention provides for a method of determining IPF prognosis in a subject, comprising measuring the levels of a set of at least three of the markers listed in Table 1 and Table 2. For those markers with a positive Cox score, increased expression (relative to control values) correlates with shorter survival while decreased expression indicates longer survival. For those markers with a negative Cox score, increased expression (relative to control values) correlates with longer survival while decreased expression indicates shorter survival.

In particular non-limiting embodiments, increases (relative to control values) in the levels of CD28, ITK, ICOS, or LCK indicate slowly progressing IPF and longer expected survival. In a first set of non-limiting embodiments, the present invention provides for a method of determining IPF prognosis in a subject, comprising measuring the levels of a set of at least three of the markers listed in Table 1 and Table 2, wherein increases (relative to control values) in the levels of CD28, ITK, ICOS, or LCK indicate slowly progressing IPF and longer expected survival.

An "increase" as that term is used herein means an increase of at least about 25% or of at least about 50% relative to control (normal plasma/plasma) values or to the mean of a plurality of normal values. A "decrease" as that term is used herein means a decrease of at least about 25% or of at least about 50% relative to control (normal plasma) values or to the mean of a plurality of normal values.

After determining the prognosis, the patient may then be advised regarding the prognosis and options for treatment (e.g. transplant), and may optionally receive one or more further diagnostic step (e.g., broncheolar lavage or biopsy) and/or treatment (e.g., lung transplant).

In one set of non-limiting embodiments, the present invention provides for a kit comprising one or more probes, such as those used in assays including, but not limited to, microarray analysis, qRT-PCR, ELISA, or Western blots, e.g., labeled or unlabeled antibody or nucleic acid probes, for determining the expression level of at least three of the markers listed in Table 1 and Table 2. In another set of non-limiting embodiments, the present invention provides for a kit comprising a one or more probes for determining the plasma levels of a panel of markers comprising CD28, ITK, ICOS, and LCK.

In one set of non-limiting embodiments, the present invention provides for a kit comprising one or more probes for determining the expression level of at least three of the markers listed in Table 1. In another set of non-limiting embodiments, the present invention provides for a kit comprising one or more probes for determining the expression level of at least three of the markers listed in Table 2. In a further set of non-limiting embodiments, the present invention provides for a kit comprising one or more probes for determining the expression level of markers comprising CD28, ITK, ICOS, and LCK.

In an alternative set of non-limiting embodiments, the present invention provides for a kit comprising one or more probes for determining the expression level of at least five of the markers listed in Table 1. In another set of non-limiting embodiments, the present invention provides for a kit comprising one or more probes for determining the expression level of at least five of the markers listed in Table 2. In a further set of non-limiting embodiments, the present invention provides for a kit comprising one or more probes for determining the expression level of markers comprising CD28, ITK, ICOS, and LCK and at least two additional markers from Table 2.

In another set of non-limiting embodiments, the present invention provides for a kit comprising one or more probes for determining the plasma levels of a panel of markers comprising CD28, ITK, ICOS, or LCK and at least two, at least three, at least four, at least five, at least six, at least seven, at least eight, at least nine, or at least ten, or at least fifteen, or at least twenty, markers selected from the Table 1 and Table 2.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the description herein. It should be understood, however, that the detailed description and the specific examples, while indicating preferred embodiments of the invention, are given by way of illustration only, since various changes and modifications within the spirit and scope of the invention will become apparent to those skilled in the art from this detailed description.

EXAMPLES

Methods

Population

Microarray studies were performed in a derivation cohort of IPF subjects evaluated at the University of Chicago (N=45) and results were validated in a replication cohort of IPF subjects evaluated at the University of Pittsburgh (N=75). qRT-PCR studies were performed in a cohort (N=139) including 43 and 74 IPF subjects from the derivation and replication cohorts respectively, and 22 additional IPF subjects evaluated at the University of Chicago. Flow cytometry studies were performed in IPF subjects (N=20) evaluated at the University of Pittsburgh. IPF diagnosis was established by a multidisciplinary group at each institution using ATS/ERS criteria[26] and it was consistent with recent guidelines (see supplementary methods).[1]

The primary time-to-event outcome analyzed was overall survival (survival); subjects were followed in clinics (at 3 to 4-month intervals) from blood draw until death, or censoring on Jun. 30, 2010; the patients who had a lung transplant during follow up were censored at transplant date. For transplant free survival, the secondary time-to-event outcome, transplants and deaths were both counted as events.

IPF diagnosis was established by a multidisciplinary group of pulmonologist, radiologist, pathologist, and rheumatologist at both institutions using ATS/ERS criteria[20] and it was consistent with recent guidelines.[1] Subjects were excluded of the study if they had evidence of autoimmune syndromes, malignancies, infections, drugs, or occupational exposures known to cause lung fibrosis. The studies were approved by the institutional review boards, and informed consent was obtained from all subjects.

Microarray Experiments, Derivation Cohort
(University of Chicago)

PBMC were obtained by density centrifugation. RNA was extracted using TRIzol (Invitrogen, Carlsbad, Calif.) and labeling reactions were performed using a GeneChip WT cDNA Synthesis and Amplification Kit, followed by hybridization using GeneChip Human 1.0 exon ST arrays (Affymetrix, Santa Clara, Calif.) following the manufacturer's protocol. Data was processed using dChip software (http://www.bioinformatics.org/dchip) and normalized by Robust Multi-array Analysis.[27]

More particularly, PBMC were obtained by Ficoll density centrifugation from blood obtained by venous phlebotomy from each subject. After washing, the PBMC were suspended on TRIzol (Invitrogen, Carlsbad, Calif.) and RNA extracted following the manufacturer's protocol. RNA yield and quality was evaluated using NanoDrop at 260 nm and the 2100 Bioanalyzer (Agilent Technologies, Santa Clara, Calif.) and specimens were stored at −70° C. for later use. Labeling reactions for microarray generation were performed using a GeneChip WT cDNA Synthesis and Amplification Kit (Affymetrix, Santa Clara, Calif.). In brief, a ribosomal RNA reduction step was performed on 1 μg of total RNA followed by cDNA synthesis with random hexamers tagged with a T7 promoter sequence. The double stranded cDNA product was then used as a template for T7 RNA polymerase amplification to produce copies of antisense cRNA. Random hexamers were used to prime reverse transcription of the cRNA from the first cycle to produce single-stranded DNA in the sense orientation using dUTP incorporation to increase the reproducibility of the fragmentation. The single-stranded DNA was then treated with a combination of uracil DNA glycosylase and apurinic/apyrimidinic endonuclease 1 to break the DNA strand. In turn, these strands were biotinylated by use of terminal deoxynucleotidyl transferase (TdT) with the Affymetrix proprietary DNA Labeling Reagent. Labeling efficiency was evaluated using the Gel-Shift Assay. The labeled single stranded DNA was hybridized using GeneChip Human 1.0 exon ST arrays (Affymetrix, Santa Clara, Calif.) and scanned using the Affymetrix GeneChip Scanner 3000, following the manufacturer's protocol. Data were processed using dChip software (http://www.bioinformatics.org/dchip). Briefly, after whole array quintile normalization using Robust Multi-array Analysis,[27] the exon intensities were summarized into gene expression levels by mapping exon probe sets into U133_Plus_2 consensus or exemplar sequences based on Affymetrix annotation U133 Plus Vs Hu Ex (03/09). Microarray experiments, replication cohort (University of Pittsburgh)

PBMC were obtained by density centrifugation. Total RNA was extracted using QIAzol (Qiagen, Valencia, Calif.) and labeling reactions were performed using Agilent Low RNA Input Linear Amplification Kit PLUS, One-Color, followed by hybridization using Whole Human Genome Oligo Microarray, 4×44K (G4112F, Agilent Technologies) following the manufacturers protocol. To normalize the gProcessed signal, cyclic-LOESS was performed using the bioconductor package as described previously.[28] Microarray experiments were compliant with MIAME guidelines. The complete datasets are available in the Gene Expression Omnibus database (http://www.ncbi.nlm.nih.gov/geo/; accession number GSE28221)

More particularly, peripheral blood was collected in a cell preparation tube (CPT), followed by centrifugation to isolate PBMC, these cells were suspended in QIAzol (Qiagen, Valencia, Calif.) and stored at −80° C. Total RNA was extracted and purified using the miRNeasy Mini Kit (Qiagen), and QIAcube device (Qiagen), following the manufacturers protocol. After extraction, total RNA yield and quality were evaluated using NanoDrop at 260 nm and the 2100 Bioanalyzer (Agilent Technologies, Santa Clara, Calif.). Labeling reactions were performed using Agilent Low RNA Input Linear Amplification Kit PLUS, One-Color (Agilent Technologies). Briefly, an initial cDNA strand was synthesized using 400 nanograms of total RNA and an oligo(dT)24 primer containing T7 RNA polymerase. This cDNA was then used as a template to generate Cy3 labeled cRNA by a reverse transcriptase enzyme. The cRNA was fragmented, hybridized to Whole Human Genome Oligo Microarray, 4×44K (G4112F, Agilent Technologies), and scanned using an Agilent Microarray Scanner. For array readout, Agilent Feature Extraction software version 10.7 was used.[41] To normalize the gProcessed signal, cyclic-LOESS was performed using the bioconductor package as described previously.[28] The average of the gene expression signal was used in the case of replicated probes for the same gene with different expression values.

qRT-PCR Experiments

A multi-sample high-throughput qRT-PCR assay was designed based on the Wafergen 5K SmartChip (Wafergen, Freemont, Calif.) which consist of a 5K SmartChip (5184 wells) preloaded with PCR primers for the genes CD28, ITK, ICOS and the endogenous control ACTB. The starting total RNA concentration was 150 ng per sample to generate cDNA that was combined with LightCycler SYBR I green master mix (Roche Applied Science, Indianapolis, Ind.) and dispensed in each well using the customized IDEX/Innovadyne Nanodrop system (Rohnert Park, Calif.). Thermocycler conditions for the PCR were: 95 degrees for 180 sec, for 40 cycles: 95 degrees for 60 sec, 60 degrees for 70 sec, Melt: 0.4 degrees/step to 95 degrees. ΔCT values were calculated by subtracting the threshold cycles of each gene target and replicates, to the threshold cycles of ACTB.

More particularly, a custom multi-sample high-throughput qRT-PCR assay was designed based on the Wafergen 5K SmartChip (Wafergen, Freemont, Calif.). In brief, this system consisted of a 5K SmartChip (5184 wells) that was preloaded with PCR primers for the genes CD28, ITK, ICOS, and ACTB. Forward and reverse primers for these genes were designed using the Universal ProbeLibrary System (Roche Applied Science, Indianapolis, Ind.) based on the Primer3 software program. Each chip was set to have 46 samples, one positive control (universal cDNA) and one negative control (NTC) with the primers in four replicates printed for each one of the samples by the manufacturing group. All primers preloaded on SmartChips were verified using human universal reference total RNA in conjunction with a two-step qPCR assay. The starting total RNA concentration was 150 ng per sample to generate cDNA using the High Capacity cDNA Reverse Transcription Kit (Applied Biosystems, Carlsbad, Calif.) following the manufacturer's protocol. The cDNA (100 pg) was combined with LightCycler SYBR I green master mix (Roche Applied Science, Indianapolis, Ind.) and dispensed in each well using the customized IDEX/Innovadyne Nanodrop system (Rohnert Park, Calif.). SmartChip thermocycler conditions for the PCR were: 95 degrees for 180 sec, for 40 cycles: 95 degrees for 60 sec, 60 degrees for 70 sec, Melt: 0.4 degrees/step to 95 degrees. qRT-PCR was not performed in two IPF subjects from the derivation and one IPF subject from the replication cohort because RNA samples were exhausted for these individuals.

Flow Cytometry Experiments

Flow cytometry methods have been previously detailed.[12] In brief, freshly isolated PBMC were stained with anti-human CD4-allophycocyanin and anti-human CD28-fluorescein isothiocyanate MAb. Individual aliquots of these cells were also stained with phycoerythrin conjugated MAb against other cell surface epitopes of interest (ICOS and CD3E in 20 IPF subjects) and these expressions were immediately determined by flow cytometery. Transcription factors (ITK and LCK in 16 IPF subjects) were determined among identical PBMC aliquots that were similarly stained with anti-human CD4 and CD28 MAb.

More particularly, freshly isolated PBMC were stained with anti-human CD4-allophycocyanin (APC) and anti-human CD28-fluorescein isothiocyanate (FITC) MAb. Individual aliquots of these cells were also stained with phycoerythrin (PE)-conjugated MAb against other cell surface epitopes of interest (ICOS and CD3E in 20 consecutive IPF individuals) and these expressions were immediately determined by flow cytometery. Transcription factors (ITK and LCK in 16 IPF subjects) were determined among identical PBMC aliquots that were similarly stained with anti-human CD4 and CD28 MAb, and fixed and permeabilized using reagents and products supplied in a kit (Cytofix/Cytoperm, BD Bioscience, San Jose, Calif.), prior to incubation with MAb having specificities for these intracellular molecules. MAb, including isotype control antibodies, were purchased from BD Bioscience (San Jose, Calif.).

Flow cytometry characterizations were performed on ≥10,000 live cells using a BD FACSCalibur (BD Bioscience). Gates for quantitative analyses were set using control fluorochrome positive and negative PBMC, including isotype controls. Unless otherwise denoted, data are delineated as percentages of cells within the respective autologous $CD4^+$ $CD28^+$ and $CD4^+CD28^{null}$ subpopulations that express the phenotypic characteristic(s) of interest. Because absolute values of mean fluorescent intensities (MFI) can vary somewhat from day to day, even using the same flow cytometer and despite appropriate calibration, cell surface CD3E MFI expression is depicted as a ratio of autologous, concurrent $CD4^+CD28^{null}/CD4^+CD28^+$ values.

Statistical Analyses

A matched gene expression dataset containing 17417 unique gene probes in each cohort was used for statistical analyses (see supplementary methods). Significance analysis of microarrays (SAM) with censored survival data[29] was used to test the association between PBMC microarray gene expression and censored survival data in IPF subjects from the derivation cohort. A stringent cutoff for gene selection (FDR<0.01) was used. For validation, hierarchical clustering using cluster 3[30] was performed in the replication cohort dataset by using the survival associated genes with FDR<0.01 identified in the derivation cohort.

Gene-set information was collected using Biocarta. 217 gene-sets containing at least six but not more than 87 genes were tested. The gene set analysis (GSA) method with censored survival data[31] was used to evaluate the association between gene-sets and censored survival data in IPF subjects in the derivation cohort and results were validated in the replication cohort. Gene-set significance was defined as P<0.05 and FDR<0.5

The SmartChip qRT-PCR ΔCt values obtained from each gene were analyzed using the survival package[32] of the R environment.[33] ΔCt values obtained from each gene were dichotomized into high- and low-risk ranges using profile likelihood.[34] The profile likelihood was maximized for each threshold and the threshold yielding the highest maximized profile likelihood was chosen for each gene separately for survival and transplant free survival. The stepAIC[35] approach was applied for variable selection to fit a multivariate Cox Proportional Hazard model (CoxPH) including ΔCt risk thresholds of CD28, ITK and ICOS along with known clinical and demographic predictors of outcome in IPF such as gender, age (dichotomized at 62 years) and baseline FVC % (dichotomized at 68% predicted). By using receiver operating characteristics (ROC) curves, the area under the curve (AUC) of this model was tested at different time points (0.25, 0.5, 0.9, 1.25, 1.5 and 2 years). The comparison of the studied T cell co-stimulatory proteins ICOS, ITK, LCK, and CD3E between CD4+CD28+ and CD4+CD28null cells was performed using the Wilcoxon test for paired samples.

Differences in age and pulmonary function tests between IPF subjects were evaluated with an unpaired, two tailed, T-test. Differences in gender, smoking status, diagnostic strategy, and use of immunosuppressive therapy were evaluated using Fisher's exact test.

Given the differences in microarray technologies between the studied cohorts (derivation cohort—Affymetrix and replication cohort—Agilent) a matched gene expression dataset was generated for statistical analyses containing 17417 unique gene probes. After each microarray platform normalization, the Affymetrix microarray gene expression dataset (N=44280 probes) was matched with the Agilent microarray gene expression dataset (N=29807 probes) by their corresponding gene ID's (http://www.ncbi.nlm.nih.gov/gene). Since there are multiple replicated probes for the same gene in the platforms studied, after microarray normalization and probe matching, the probes were selected with the highest Inter Quartile Range (IQR) variation across the arrays (N=17417 unique gene probes) and each independent dataset was used for analyses.

We used significance analysis of microarrays (SAM) with censored survival data[29] to test the association between PBMC microarray gene expression values and censored survival data in IPF subjects from the derivation cohort. SAM computes a Cox score test for each gene; a positive score indicates that higher expression correlates with higher risk (i.e shorter survival) while lower expression indicates lower risk (i.e longer survival) and a negative score indicates that higher expression correlates with lower risk (i.e. longer survival) while lower expression correlates with higher risk (i.e shorter survival). SAM also performs permutations of the censored survival data of each individual to calculate the false discovery rate (FDR); 100 permutations were used to identify a survival gene signature. Significance was defined as a FDR<0.05, although a stringent cutoff of FDR<0.01 was used for gene selection. Hierarchical clustering using cluster 3[30] was performed in the replication cohort dataset by using the survival associated genes with FDR<0.01 previously identified in the derivation cohort. The genes were centered by the median and genes and arrays were clustered using complete linkage and centered correlation.

We also collected gene-set information using Biocarta. 217 gene-sets containing at least six but not more than 87 genes were tested in the derivation and replication cohorts. The gene set analysis (GSA) method with censored survival data[31] was used to evaluate the association between gene-sets and censored survival data in IPF subjects in each independent microarray cohort. GSA calculates a Cox score test for each gene and then uses the Maxmean summary statistic; this is the mean of the positive or negative part of gene scores in the gene-set, whichever is large in absolute values. A negative gene-set is one in which lower expression of most genes in the gene set correlates with higher risk (i.e shorter survival) and a positive gene-set is one in which lower expression of most genes in the gene set correlates with higher risk (i.e shorter survival). GSA also performs permutations of the censored survival data of each individual to calculate the false discovery rate (FDR); 1000 permutations were used to identify statistically significant gene-sets. Gene-set significance was defined as P<0.05 and FDR<0.5

The SmartChip qRT-PCR ΔCt values obtained from each gene were analyzed using the survival package[32] of the R environment.[33] ΔCt values obtained from each gene were dichotomized into high- and low-risk ranges using profile likelihood.[34] The profile likelihood was maximized for each threshold and the threshold yielding the highest maximized profile likelihood was chosen for each gene separately for survival and transplant free survival. The ΔCt risk thresholds of CD28, ITK, ICOS, and LCK, obtained from profile likelihood (there being only finitely many possible thresholds based on the observed data), were used as a parameter in a Cox proportional hazards (CoxPH) model to adjust each gene to known clinical and demographic predictors of outcome in IPF such as gender, age (dichotomized at 62 years) and baseline FVC % (dichotomized at 68% predicted). Differences in survival were evaluated using the logrank test and results were shown using Kaplan Meier curves. Lastly, the stepAIC[35] approach was applied for variable selection in a multivariate CoxPH model to fit CD28, ITK, ICOS, age, gender, and FVC % in an attempt to identify the best prediction model for survival and transplant free survival. By using receiver operating characteristics (ROC) curves, the Area Under the Curve (AUC) of this model was tested, which estimates the probability that between two randomly selected patients, the patient with the higher predicted risk of dying (in the case of survival) or dying and having a lung transplant (in the case of transplant free survival) will be the first to have the studied outcome and this probability was computed at different time points (0.25, 0.5, 0.9, 1.25, 1.5 and 2 years).

The comparison of the studied T-cell co-stimulatory proteins ICOS, ITK, LCK, and CD3E between CD4+CD28+ and CD4+CD28null cells was performed using the Wilcoxon test for paired samples.

Differences in age and pulmonary function tests between IPF subjects were evaluated with an unpaired, two tailed, T-test. Differences in gender, smoking status, diagnostic strategy, and use of immunosuppressive therapy were evaluated using Fisher's exact test.

Given the differences in microarray technologies between the studied cohorts (derivation cohort—Affymetrix and replication cohort—Agilent) a matched gene expression dataset was generated for statistical analyses containing 17417 unique gene probes. After each microarray platform normalization, the Affymetrix microarray gene expression dataset (N=44280 probes) was matched with the Agilent microarray gene expression dataset (N=29807 probes) by their corresponding gene ID's (http://www.ncbi.nlm.nih.gov/gene). Since there are multiple replicated probes for the same gene in the platforms studied, after microarray normalization and probe matching, the probes with the highest Inter Quartile Range (IQR) variation across the arrays (N=17417 unique gene probes) were selected and each independent dataset was used for analyses.

We used significance analysis of microarrays (SAM) with censored survival data 29 to test the association between PBMC microarray gene expression values and censored survival data in IPF subjects from the derivation cohort. SAM computes a Cox score test for each gene; a positive score indicates that higher expression correlates with higher risk (i.e shorter survival) while lower expression indicates lower risk (i.e longer survival) and a negative score indicates that higher expression correlates with lower risk (i.e. longer survival) while lower expression correlates with higher risk (i.e shorter survival). SAM also performs permutations of the censored survival data of each individual to calculate the false discovery rate (FDR); 100 permutations were used to identify a survival gene signature. Significance was defined as a FDR<0.05, although a stringent cutoff of FDR<0.01 was used for gene selection. Hierarchical clustering using cluster 3 30 was performed in the replication cohort dataset by using the survival associated genes with FDR<0.01 previously identified in the derivation cohort. The genes were centered by the median and genes and arrays were clustered using complete linkage and centered correlation.

Gene-set information was also collected using Biocarta. 217 gene-sets containing at least six but not more than 87 genes were tested in the derivation and replication cohorts. The gene set analysis (GSA) method with censored survival data 31 was used to evaluate the association between gene-sets and censored survival data in IPF subjects in each independent microarray cohort. GSA calculates a Cox score test for each gene and then uses the Maxmean summary statistic; this is the mean of the positive or negative part of gene scores in the gene-set, whichever is large in absolute values. A negative gene-set is one in which lower expression of most genes in the gene set correlates with higher risk (i.e shorter survival) and a positive gene-set is one in which lower expression of most genes in the gene set correlates with higher risk (i.e shorter survival). GSA also performs permutations of the censored survival data of each individual to calculate the false discovery rate (FDR); 1000 permutations were used to identify statistically significant gene-sets. Gene-set significance was defined as P<0.05 and FDR<0.5

The SmartChip qRT-PCR ΔCt values obtained from each gene were analyzed using the survival package 32 of the R environment. 33 ΔCt values obtained from each gene were dichotomized into high- and low-risk ranges using profile likelihood. 34 The profile likelihood was maximized for each threshold and the threshold yielding the highest maximized profile likelihood was chosen for each gene separately for survival and transplant free survival. The ΔCt risk thresholds of CD28, ITK, ICOS, and LCK, obtained from profile likelihood (there being only finitely many possible thresholds based on the observed data), were used as a parameter in a Cox proportional hazards (CoxPH) model to adjust each gene to known clinical and demographic predictors of outcome in IPF such as gender, age (dichotomized at 62 years) and baseline FVC % (dichotomized at 68% predicted). Differences in survival were evaluated using the logrank test and results were shown using Kaplan Meier curves. Lastly, the stepAIC 35 approach was applied for variable selection in a multivariate CoxPH model to fit CD28, ITK, ICOS, age, gender, and FVC % in an attempt to identify the best prediction model for survival and transplant free survival. By using receiver operating characteristics (ROC) curves, the Area Under the Curve (AUC) of this model was tested, which estimates the probability that between two randomly selected patients, the patient with the higher predicted risk of dying (in the case of survival) or dying and having a lung transplant (in the case of transplant free survival) will be the first to have the studied outcome and this probability was computed at different time points (0.25, 0.5, 0.9, 1.25, 1.5 and 2 years).

The comparison of the studied T-cell co-stimulatory proteins ICOS, ITK, LCK, and CD3E between CD4+CD28+ and CD4+CD28null cells was performed using the Wilcoxon test for paired samples.

Results

Characteristics of the Patients

The microarray derivation and replication cohort were comparable with the exception of gender, race, and lung transplants. Lung biopsy confirmed the finding of usual interstitial pneumonia (UIP) in 63.3% of the cases and only a small proportion of patients (9.3%) were on immunosuppressant agents at blood draw.

Microarray Analyses Demonstrate a 38-Gene Signature and the T-Cell Co-Stimulatory Pathway Associated with Survival in the Derivation Cohort Thirty eight genes (N=38) were significantly associated with survival in the derivation cohort (FDR<0.01). The majority of these genes (N=29) had a negative score, with the lowest score indicating shorter survival while nine genes (N=9) had a positive score, with the highest score indicating shorter survival (Table 1). This 38-gene signature provided clues about potential biological process associated with survival in IPF given the presence of many T-cell related genes (especially in the negative score group); this led us to study more deeply the potential association of pathways with survival by using a survival gene-set analysis in the derivation cohort, which identified the co-stimulatory signal during T-cell activation pathway (Tables 4 and S2) as the gene-set with the lowest score and P value (score −1.74, P=0.004, FDR=0.45), indicating that lower expression of most genes in this gene-set were correlated with shorter survival. ITK, CD28, and ICOS had the lowest score within the T-cell co-stimulatory signaling pathway (Table 2) and were also part of the 38-gene survival signature.

Microarray Analyses Validate the 38-Gene Signature and T-Cell Co-Stimulatory Pathway Association with Survival in the Replication Cohort To validate the 38-gene signature identified in the derivation cohort, hierarchical clustering of these genes and arrays in the replication cohort was performed, demonstrating two major clusters of IPF subjects (FIG. 1, panel A) with significant differences in survival (hazard ratio 3.16, 95% CI 1.23-8.07, P=0.006) (FIG. 1, panel B) and without significant clinical and epidemiological differences (Table S1). The median survival of subjects in cluster two was 2.01 years while survival in cluster one subjects was much greater and median levels were not reached. To confirm the presence of pathways associated with survival in the replication cohort the survival gene-set analysis was performed and again, the co-stimulatory signal during T-cell activation pathway (FIG. 1, panel C) had the lowest score and P value (score −1.34, P=0.008, FDR=0.42) from the negative gene-set group (Table S3). As evidenced in the derivation cohort CD28, ITK, ICOS, and LCK were also the genes with the lowest score within the pathway (FIG. 1, panel C).

SmartChip qRT-PCR confirms that decreases in PBMC CD28, ITK, ICOS, and LCK expression are associated with poor outcomes in IPF.

Figure 2:
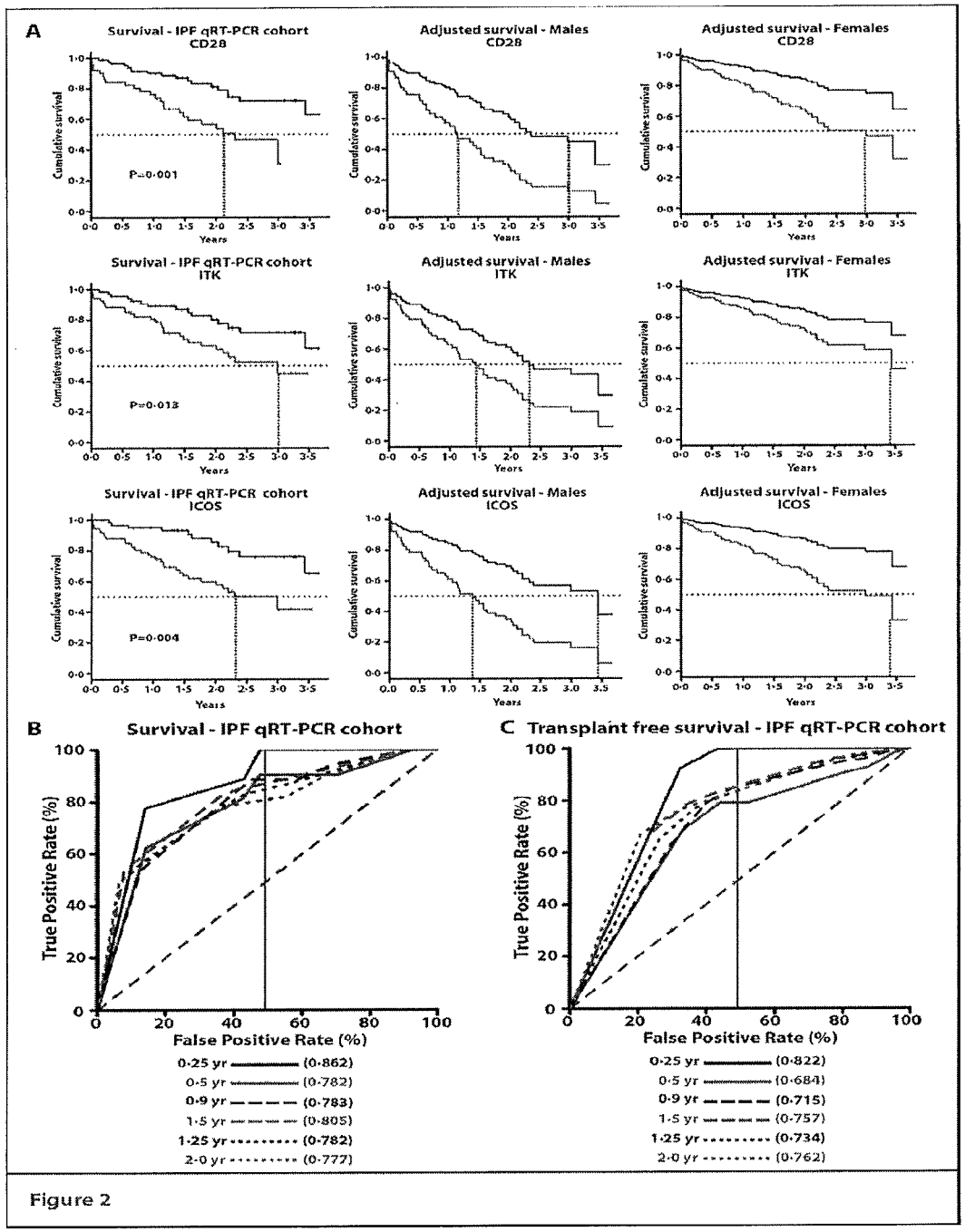
FIG. 2. SmartChip qRT-PCR survival analysis based on ΔCt expression values (using actin B as the endogenous control) of CD28, ITK, ICOS, and LCK in a cohort of 139 IPF subjects (Panel A). Gray line—patients with expression levels above the threshold ΔCt (representing a decrease in gene expression). Black line—patients with expression levels below the threshold ΔCt (representing an increase in gene expression). Kaplan-Meier plots are shown for each gene in the unified cohort as well as age and FVC % adjusted in males and females separately. Panel B and C depicts the ROC curve of a CoxPH model that fits the dichotomized ΔCt thresholds of CD28 along with age, gender and FVC % for estimating survival and transplant free survival predictions at various time points (different line colors) after blood draw. The AUC for each plot is shown in parentheses.
Figure 3:
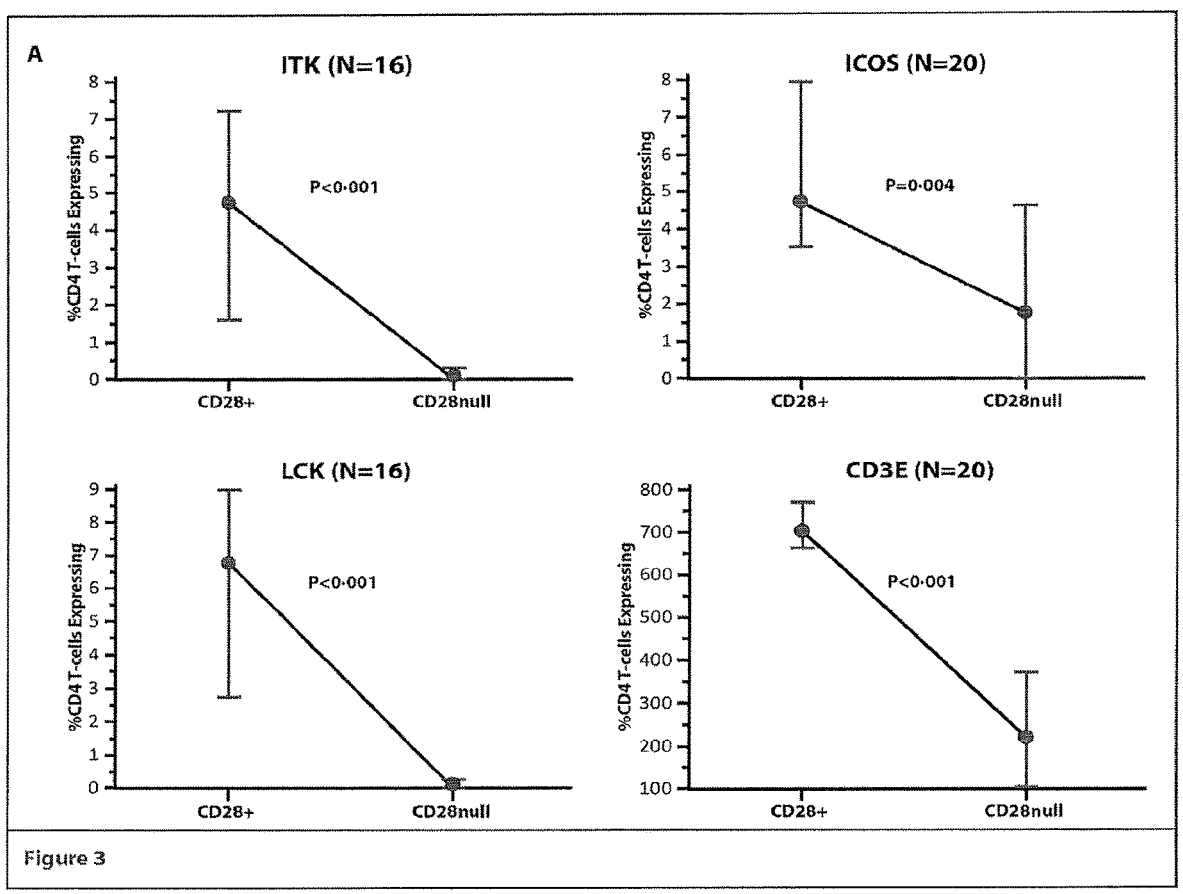
FIG. 3. The graphics represent the paired percentage of CD4+CD28+ and CD4+CD28null cells expression of T-cell co-stimulatory proteins ITK, ICOS, LCK, and CD3E in IPF subjects evaluated at the University of Pittsburgh. Gray dot—median, gray lines—error bars (95% CI for a median), black lines—connecting lines between the paired samples.

A custom SmartChip qRT-PCR assay was designed to evaluate the performance and prognostic significance of the T-cell co-stimulatory signaling pathway genes CD28, ITK, ICOS, and LCK in a more clinically feasible platform. ΔCt values for CD28, ITK, ICOS, and LCK above the calculated threshold (split at 6.112, 5.600, and 6.939 cycles respectively, for survival) and thereby indicative of reduced gene expression, were significantly associated with lesser median survival (2.3, 2.9, and 2.9 years, respectively). Conversely, lower ΔCt values (denoting greater gene expression) were predictive of longer median survival in the qRT-PCR cohort (N=139) (FIG. 2, panel A). This effect was much more evident in males older than 62 years with a FVC % below 68%. Decrease in CD28, ITK, ICOS, and LCK expression in this subgroup was associated with significantly lower median survival (1.12-1.42 years) and increased expression was predictive of significantly longer median survival (2.31-3.46 years). The shortest median survival in older males with low FVC % was seen with low CD28 (1.12 years, ΔCt above 6.112) and low ICOS (1.38 years, ΔCt above 6939) and the longest median survival (3.46 years) was seen with increased ICOS (ΔCt below 6.939). The adjusted hazard ratios to age, gender, and FVC % for all subjects were generally similar for CD28, ITK, ICOS, and LCK (2.57, 2.00, and 2.88 respectively) meaning that low level of expression of these genes at evaluation, was associated with at least two-fold higher risk of death. A multivariate CoxPH model including ΔCt expression of CD28 (split at 6.112 for survival and 4.673 for transplant free survival), age (split at 62 years), gender, and FVC % (split at 68%) showed an accurate prediction of survival (AUC range: 77.7%-86.2%) and transplant free survival (AUC range: 68.4%-82.2%) with the highest AUC being for predicting death and transplant free survival within 3 months after blood draw (86.2% and 82.2% respectively) (FIG. 3, panels B and C).

The Down Regulation of Co-Stimulatory Molecules Can be Explained by CD4 T-Cell End-Differentiation Recent reports implicate adaptive immune processes in IPF,[12, 36, 37] in particular, repetitive CD4 T-cell activation, clonal expansion, and end-differentiation, the latter characterized by phenotypic changes including the loss of cell surface CD28, have also been associated with decreased survival of IPF patients.[12] In order to examine the possibility that gene down-regulations of the T-cell co-stimulatory signaling pathway found here may be related to T-cell activation and differentiation, protein levels of the T-cell co-stimulatory signaling molecules in CD4+CD28$^{null}$ T-cells using flow cytometry were measured. The levels of members of the prognosis signature ITK, ICOS as well as the T-cell co-stimulatory members LCK, and CD3E were significantly decreased in the end-differentiated CD4+ CD28$^{null}$ cells of IPF patients, compared to autologous CD4+CD28+ cells ($P<0.001$, $P=0.004$, $P<0.001$, and $P<0.001$ respectively).

Discussion

Microarray analysis of PBMC gene expression in two cohorts of IPF subjects were evaluated and found to be concordant at two different academic institutions using two different microarray platforms. A signature of 38 genes was identified, as well as down-regulation of the T-cell co-stimulatory signaling pathway significantly associated with shorter survival in the derivation cohort. Significant differences in survival based on clustering of the 38-gene signature as well as down-regulation of the T-cell co-stimulatory signaling pathway associated with shorter survival in the replication cohort, provided validation of the findings. qRT-PCR, confirmed microarray results and indicated that IPF subjects with decreased expression of CD28, ITK, and ICOS had shorter survival, a finding that was impressively more evident among males. A combined genomic and clinical prediction model including ΔCt expression of CD28, age, gender, and FVC % provided a prediction above 80% for survival and transplant free survival within 3 months after blood draw. Finally, the T-cell co-stimulatory proteins ITK, ICOS, LCK, and CD3E were found to be decreased in CD4+CD28$^{null}$ T-cells suggesting that the gene expression findings described herein may be indicative of T-cell end-differentiation that occurs in IPF.[12, 37]

Increases in peripheral blood protein concentrations such as KL-6, surfactant protein A, CCL18, MMP7, ICAM, and IL8[8, 11, 13, 38] have all been associated with decreased survival in IPF patients. Most recently a prognostic score derived from the integration of clinical information and MMP7 concentrations has been identified and confirmed in two cohorts.[13] While previous reports based their initial search for markers on prior hypotheses or on a limited list of proteins, the largest number being 95,[13] the biomarkers described herein were derived from an unbiased genome scale screening of gene transcripts.

Another aspect that distinguishes this study from previous peripheral blood molecular marker studies in IPF is that this study focuses on PBMC, not on serum or plasma. PBMC gene expression patterns have been shown to be different from healthy controls in multiple disease classes[17, 18, 20-25] but the studies only rarely find outcome indicative signatures and their potential cellular origin. Given our previous reports of the existence of T-cell end-differentiation (transition of T cells from CD4+CD28+ to CD4+CD28$^{null}$) in IPF[37] and particularly, the increase in CD4+ CD28$^{null}$ T cells inversely associated with poor IPF outcomes,[12] we studied and confirmed diminished expression of T-cell co-stimulatory proteins among CD4+CD28$^{null}$ lymphocytes providing protein confirmation of the gene expression findings suggesting that mortality in IPF is probably not merely associated with decreases in T-cell co-stimulatory signaling pathway genes but is potentially determined by the T-cell end-differentiation process that is potentially important in disease pathogenesis.

The implications of predicting survival in IPF are significant. The only effective therapy currently available for IPF patients is lung transplantation. The timing of transplantation is determined by the clinical evaluation, as well as the lung allocation score.[39] The pre-transplant evaluation is cost-intensive and not invariably accurate enough to establish optimal timing.[40] Furthermore, shortage of organs is still a significant limitation. Hence, risk stratification based on the PBMC expression of T-cell co-stimulatory signaling pathway genes and specifically the genomic and clinical predictor model described herein could have valuable applications in determining who should be referred for pre transplantation assessments and specifically, given the ability of the model to predict early mortality, to prioritize organ allocations to those who have been evaluated. The ability to predict survival is also important for drug studies in IPF. In a relatively uncommon disease, to show an effect of a drug on mortality, investigators need to recruit patients who are likely to progress during the course of the study. The relative accurate prediction of early death by our markers may help to recruit such patients. Additionally, because of the difficulty in clinically predicting the disease course it is possible that patients from a certain risk strata end up randomly and disproportionately assigned to one of the experimental groups leading to spurious results. Molecular based patient risk stratification will address this challenge. Finally, the use of the markers described herein is highly feasible since qRT-PCR is commonly used, easy to interpret and highly reproducible and PBMC isolation is easy to obtain and does not require sophisticated immunological methods.

Genomic biomarker studies often cannot be replicated. In our case while the cohorts were relatively similar clinically, there were some significant differences that could have prevented the replication. Gene expression analysis was performed on two different platforms, the practice patterns are very different in the two institutions and most critically the rate of lung transplantations (Table 1) was overtly varied. Despite these limitations we were able to replicate our results and demonstrate that both the 38-gene signature and the T-cell co-stimulatory signaling pathway predicted survival in both cohorts. In this context it is important to note that it is possible that these differences may have affected our ability to detect signals for more granular disease subphenotypes, such as pulmonary hypertension, disease progression or impending acute exacerbations. Larger studies will be required to determine whether PBMC gene expression patterns are also predictive of these phenotypes.

CD28, ITK, and ICOS gene expression was sufficient to identify IPF patients destined for poor outcomes and thus could have considerable value in clinical evaluations, and management of patients with this morbid lung disease; naturally, despite the marked reproducibility of our findings across two cohorts, additional studies focused on validating our results will be required before PBMC gene expression can be used clinically for prognosis determination.

Each of the publications cited herein is incorporated by reference in its entirety.

1. Raghu G, Collard H R, Egan J J, et al. An official ATS/ERS/JRS/ALAT statement: idiopathic pulmonary fibrosis: evidence-based guidelines for diagnosis and management. *American journal of respiratory and critical care medicine* 2011; 183 (6): 788-824.
2. Fernandez Perez E R, Daniels C E, Schroeder D R, et al. Incidence, prevalence, and clinical course of idiopathic pulmonary fibrosis: a population-based study. *Chest* 2010; 137 (1): 129-37.
3. Schwartz D A, Helmers R A, Galvin J R, et al. Determinants of survival in idiopathic pulmonary fibrosis. *American journal of respiratory and critical care medicine* 1994; 149(2 Pt 1): 450-4.
4. King T E, Jr., Tooze J A, Schwarz M I, Brown K R, Cherniack R M. Predicting survival in idiopathic pulmonary fibrosis: scoring system and survival model. *American journal of respiratory and critical care medicine* 2001; 164 (7): 1171-81.
5. Zappala C J, Latsi P I, Nicholson A G, et al. Marginal decline in forced vital capacity is associated with a poor outcome in idiopathic pulmonary fibrosis. *Eur Respir J* 2010; 35 (4): 830-6.
6. Ley B, Collard H R, King T E, Jr. Clinical course and prediction of survival in idiopathic pulmonary fibrosis. *American journal of respiratory and critical care medicine* 2011; 183 (4): 431-40.
7. du Bois R M, Weycker D, Albera C, et al. Forced vital capacity in patients with idiopathic pulmonary fibrosis: test properties and minimal clinically important difference. *American journal of respiratory and critical care medicine* 2011; 184 (12): 1382-9.
8. Rosas I O, Richards T J, Konishi K, et al. MMP1 and MMP7 as potential peripheral blood biomarkers in idiopathic pulmonary fibrosis. *PLoS medicine* 2008; 5 (4): e93.
9. Moeller A, Gilpin S E, Ask K, et al. Circulating fibrocytes are an indicator of poor prognosis in idiopathic pulmonary fibrosis. *American journal of respiratory and critical care medicine* 2009; 179 (7): 588-94.
10. Prasse A, Probst C, Bargagli E, et al. Serum CC-chemokine ligand 18 concentration predicts outcome in idiopathic pulmonary fibrosis. *American journal of respiratory and critical care medicine* 2009; 179 (8): 717-23.
11. Kinder B W, Brown K K, McCormack F X, et al. Serum surfactant protein-A is a strong predictor of early mortality in idiopathic pulmonary fibrosis. *Chest* 2009; 135 (6): 1557-63.
12. Gilani S R, Vuga L J, Lindell K O, et al. CD28 down-regulation on circulating CD4 T-cells is associated with poor prognoses of patients with idiopathic pulmonary fibrosis. *PloS one* 2010; 5 (1): e8959.
13. Richards T J, Kaminski N, Baribaud F, et al. Peripheral blood proteins predict mortality in idiopathic pulmonary fibrosis. *American journal of respiratory and critical care medicine* 2012; 185 (1): 67-76.
14. Yang I V, Luna L G, Cotter J, et al. The peripheral blood transcriptome identifies the presence and extent of disease in idiopathic pulmonary fibrosis. *PloS one* 2012; 7 (6): e37708.
15. Herazo-Maya J D, Kaminski N. Personalized medicine: applying 'omics' to lung fibrosis. *Biomarkers in medicine* 2012; 6 (4): 529-40.
16. Achiron A, Gurevich M, Friedman N, Kaminski N, Mandel M. Blood transcriptional signatures of multiple sclerosis: unique gene expression of disease activity. *Annals of neurology* 2004; 55 (3): 410-7.
17. Bull T M, Coldren C D, Nana-Sinkam P, et al. Microarray analysis of peripheral blood cells in pulmonary arterial hypertension, surrogate to biopsy. *Chest* 2005; 128 (6 Suppl): 584S.
18. Moore D F, Li H, Jeffries N, et al. Using peripheral blood mononuclear cells to determine a gene expression profile of acute ischemic stroke: a pilot investigation. *Circulation* 2005; 111(2): 212-21.
19. Bluth M, Lin Y Y, Zhang H, Viterbo D, Zenilman M. Use of gene expression profiles in cells of peripheral blood to identify new molecular markers of acute pancreatitis. *Arch Surg* 2008; 143 (3): 227-33; discussion 33-4.
20. Showe M K, Vachani A, Kossenkov A V, et al. Gene expression profiles in peripheral blood mononuclear cells can distinguish patients with non-small cell lung cancer from patients with nonmalignant lung disease. *Cancer research* 2009; 69 (24): 9202-10.
21. Pham M X, Teuteberg J J, Kfoury A G, et al. Gene-expression profiling for rejection surveillance after cardiac transplantation. *The New England journal of medicine* 2010; 362 (20): 1890-900.
22. Risbano M G, Meadows C A, Coldren C D, et al. Altered immune phenotype in peripheral blood cells of patients with scleroderma-associated pulmonary hypertension. *Clin Transl Sci* 2010; 3 (5): 210-8.
23. Baine M J, Chakraborty S, Smith L M, et al. Transcriptional profiling of peripheral blood mononuclear cells in pancreatic cancer patients identifies novel genes with potential diagnostic utility. *PloS one* 2011; 6 (2): e17014.
24. Ottoboni L, Keenan B T, Tamayo P, et al. An RNA profile identifies two subsets of multiple sclerosis patients differing in disease activity. *Science translational medicine* 2012; 4 (153): 153ra31.
25. Segman R H, Shefi N, Goltser-Dubner T, Friedman N, Kaminski N, Shalev A Y. Peripheral blood mononuclear cell gene expression profiles identify emergent post-traumatic stress disorder among trauma survivors. *Molecular psychiatry* 2005; 10 (5): 500-13, 425.
26. American Thoracic S, European Respiratory S. American Thoracic Society/European Respiratory Society International Multidisciplinary Consensus Classification of the Idiopathic Interstitial Pneumonias. This joint statement of the American Thoracic Society (ATS), and the European Respiratory Society (ERS) was adopted by the ATS board of directors, June 2001 and by the ERS Executive Committee, June 2001. *American journal of respiratory and critical care medicine* 2002; 165 (2): 277-304.
27. Irizarry R A, Hobbs B, Collin F, et al. Exploration, normalization, and summaries of high density oligonucleotide array probe level data. *Biostatistics (Oxford, England)* 2003; 4 (2): 249-64.
28. Wu W, Dave N, Tseng G C, Richards T, Xing E P, Kaminski N. Comparison of normalization methods for CodeLink Bioarray data. *BMC bioinformatics* 2005; 6: 309.
29. Tusher V G, Tibshirani R, Chu G. Significance analysis of microarrays applied to the ionizing radiation response. *Proceedings of the National Academy of Sciences of the United States of America* 2001; 98 (9): 5116-21.
30. http://bonsai.hgc.jp/~mdehoon/software/cluster/manual.
31. Efron B, Tibshirani R. On testing the significance of set of genes. *Ann App Stat* 2007; 1 (1): 107-29.

32. Therneau T M G P. Modeling survival data: extending the Cox model. New York: Springer; 2000.
33. Ihaka R G R. A language for data analysis and graphics. *J Comput Graph Statist* 1996; 5: 299-314.
34. Murphy S A, Van Der Vart A W. On Profile Likelihood. *Journal of the American Statistical Association* 2000; 95: 449-85.
35. Venables W N R, B. D. Modern applied statistics with S. New York: Springer; 2002.
36. Xue J, Gochuico B R, Alawad A S, et al. The HLA class II Allele DRB1*1501 is over-represented in patients with idiopathic pulmonary fibrosis. *PloS one* 2011; 6 (2): e14715.
37. Feghali-Bostwick C A, Tsai C G, Valentine V G, et al. Cellular and humoral autoreactivity in idiopathic pulmonary fibrosis. *J Immunol* 2007; 179 (4): 2592-9.
38. Yokoyama A, Kondo K, Nakajima M, et al. Prognostic value of circulating KL-6 in idiopathic pulmonary fibrosis. *Respirology (Carlton, Vic* 2006; 11 (2): 164-8.
39. Egan T M, Murray S, Bustami R T, et al. Development of the new lung allocation system in the United States. *Am J Transplant* 2006; 6 (5 Pt 2): 1212-27.
40. Trulock E P, Edwards L B, Taylor D O, Boucek M M, Keck B M, Hertz M I. Registry of the International Society for Heart and Lung Transplantation: twenty-second official adult lung and heart-lung transplant report—2005. *J Heart Lung Transplant* 2005; 24 (8): 956-67.
41. Zahurak M, Parmigiani G, Yu W, et al. Pre-processing Agilent microarray data. *BMC bioinformatics* 2007; 8: 142.

The invention claimed is:

1. A method for detecting CD28, ITK, ICOS, and LCK in an individual diagnosed with idiopathic pulmonary fibrosis (IPF) comprising:
   obtaining a biological sample from a human individual; and
   detecting expression levels of a set of biomarkers in the sample from the individual by performing ELISA or Western blot and detecting biomarker protein, wherein the biomarkers comprise CD28, ITK, ICOS, and LCK.
2. The method of claim 1, wherein the sample comprises nucleated cells.
3. The method of claim 2, wherein the cells are lung cells.
4. The method of claim 2, wherein the cells are peripheral blood mononuclear cells.
5. The method of claim 1, wherein the sample is a serum or plasma sample.
6. A method involving an individual being treated with an IPF therapeutic, the method comprising assaying for the expression level of CD28, ITK, ICOS, and LCK in a biological sample from the individual.
7. The method of claim 6, wherein the biological sample comprises a serum or plasma sample.
8. The method of claim 6, wherein the biological sample comprises nucleated cells.
9. The method of claim 8, wherein the cells are lung cells.
10. The method of claim 8, wherein the cells are peripheral blood mononuclear cells.
11. The method of claim 6, wherein the expression levels of the biomarkers are assayed by performing ELISA or Western blot and detecting the protein biomarkers.
12. The method of claim 6, wherein the method further comprises obtaining a biological sample from the individual.

* * * * *